US011224392B2

(12) United States Patent
Krimsky (10) Patent No.: US 11,224,392 B2
(45) Date of Patent: Jan. 18, 2022

(54) MAPPING DISEASE SPREAD

(71) Applicant: Covidien LP, Mansfield, MA (US)

(72) Inventor: William S. Krimsky, Forest Hill, MD (US)

(73) Assignee: COVIDIEN LP, Mansfield, MA (US)

( * ) Notice: Subject to any disclaimer, the term of this patent is extended or adjusted under 35 U.S.C. 154(b) by 223 days.

(21) Appl. No.: 16/259,449

(22) Filed: Jan. 28, 2019

(65) Prior Publication Data

US 2019/0231287 A1 Aug. 1, 2019

Related U.S. Application Data

(60) Provisional application No. 62/624,905, filed on Feb. 1, 2018.

(51) Int. Cl.
*A61B 6/00* (2006.01)
*A61B 5/00* (2006.01)
(Continued)

(52) U.S. Cl.
CPC ............ *A61B 6/466* (2013.01); *A61B 5/0059* (2013.01); *A61B 6/037* (2013.01); *A61B 6/12* (2013.01); *A61B 6/4417* (2013.01); *A61B 6/487* (2013.01); *A61B 8/0841* (2013.01); *A61B 8/12* (2013.01); *A61B 8/4245* (2013.01); *A61B 8/4254* (2013.01); *A61B 8/4416* (2013.01); *A61B 8/463* (2013.01); *A61B 8/466* (2013.01); *A61B 8/5261* (2013.01); *G06T 7/0014* (2013.01); *G06T 7/149* (2017.01); *G16H 50/50* (2018.01); *A61B 8/085* (2013.01); *A61B 10/04* (2013.01); *A61B 2010/045* (2013.01);
(Continued)

(58) Field of Classification Search
None
See application file for complete search history.

(56) References Cited

U.S. PATENT DOCUMENTS 5,592,939 A 1/1997 Martinelli
5,611,025 A 3/1997 Lorensen et al.
(Continued)

FOREIGN PATENT DOCUMENTS

CN 1658789 A 8/2005
CN 101322652 A 12/2008
(Continued)

OTHER PUBLICATIONS

Sorger et al. "A novel platform for electromagnetic navigated ultrasound bronchoscopy (EBUS)". Int J CARS (2016) 11:1431-1443 DOI 10.1007/s11548-015-1326-7. (Year: 2015).*
(Continued)

*Primary Examiner* — Joseph M Santos Rodriguez
(74) *Attorney, Agent, or Firm* — Carter, DeLuca & Farrell LLP (57) ABSTRACT

Disclosed are systems and methods for mapping a patient's lymphatic system. An exemplary method includes generating a three-dimensional (3D) model of a bronchial network in the patient's chest, generating a lymphatic tree map by fitting a model lymph node map to the 3D model, receiving locations of a plurality of identified lymph nodes, updating the positions of lymph nodes on the lymphatic tree map, and displaying the updated lymphatic tree map.

12 Claims, 6 Drawing Sheets

(51) Int. Cl.

| | |
|---|---|
| *G16H 50/50* | (2018.01) |
| *A61B 8/00* | (2006.01) |
| *G06T 7/00* | (2017.01) |
| *G06T 7/149* | (2017.01) |
| *A61B 6/12* | (2006.01) |
| *A61B 8/08* | (2006.01) |
| *A61B 6/03* | (2006.01) |
| *A61B 8/12* | (2006.01) |
| *A61B 10/04* | (2006.01) |

(52) U.S. Cl.
CPC .......... *G06T 2207/10081* (2013.01); *G06T 2207/20128* (2013.01); *G06T 2207/30061* (2013.01)

(56) References Cited

U.S. PATENT DOCUMENTS

| | | |
|---|---|---|
| 5,676,673 A | 10/1997 | Ferre et al. |
| 5,697,377 A | 12/1997 | Wittkampf |
| 5,699,799 A | 12/1997 | Xu et al. |
| 5,715,836 A | 2/1998 | Kliegis et al. |
| 5,729,129 A | 3/1998 | Acker |
| 5,752,513 A | 5/1998 | Acker et al. |
| 5,782,762 A | 7/1998 | Vining |
| 5,881,124 A | 3/1999 | Giger et al. |
| 5,891,030 A | 4/1999 | Johnson et al. |
| 5,913,820 A | 6/1999 | Bladen et al. |
| 5,920,319 A | 7/1999 | Vining et al. |
| 5,967,980 A | 10/1999 | Ferre et al. |
| 5,971,767 A | 10/1999 | Kaufman et al. |
| 5,987,960 A | 11/1999 | Messner et al. |
| 6,019,725 A | 2/2000 | Vesely et al. |
| 6,047,080 A | 4/2000 | Chen et al. |
| 6,083,162 A | 7/2000 | Vining |
| 6,138,045 A | 10/2000 | Kupinski et al. |
| 6,151,404 A | 11/2000 | Pieper |
| 6,167,296 A | 12/2000 | Shahidi |
| 6,181,348 B1 | 1/2001 | Geiger |
| 6,201,387 B1 | 3/2001 | Govari |
| 6,233,476 B1 | 5/2001 | Strommer et al. |
| 6,246,784 B1 | 6/2001 | Summers et al. |
| 6,266,551 B1 | 7/2001 | Osadchy et al. |
| 6,332,089 B1 | 12/2001 | Acker et al. |
| 6,346,940 B1 | 2/2002 | Fukunaga |
| 6,366,800 B1 | 4/2002 | Vining et al. |
| 6,381,485 B1 | 4/2002 | Hunter et al. |
| 6,387,092 B1 | 5/2002 | Burnside et al. |
| 6,466,815 B1 | 10/2002 | Saito et al. |
| 6,496,188 B1 | 12/2002 | Deschamps et al. |
| 6,501,848 B1 | 12/2002 | Carroll et al. |
| 6,501,981 B1 | 12/2002 | Schweikard et al. |
| 6,505,065 B1 | 1/2003 | Yanof et al. |
| 6,522,907 B1 | 2/2003 | Bladen et al. |
| 6,526,162 B2 | 2/2003 | Asano et al. |
| 6,535,756 B1 | 3/2003 | Simon et al. |
| 6,578,579 B2 | 6/2003 | Burnside et al. |
| 6,584,174 B2 | 6/2003 | Schubert et al. |
| 6,603,868 B1 | 8/2003 | Ludwig et al. |
| 6,611,793 B1 | 8/2003 | Burnside et al. |
| 6,650,927 B1 | 11/2003 | Keidar |
| 6,651,669 B1 | 11/2003 | Burnside |
| 6,694,163 B1 | 2/2004 | Vining |
| 6,757,557 B1 | 6/2004 | Bladen et al. |
| 6,783,523 B2 | 8/2004 | Qin et al. |
| 6,792,390 B1 | 9/2004 | Burnside et al. |
| 6,829,379 B1 | 12/2004 | Knoplioch et al. |
| 6,850,794 B2 | 2/2005 | Shahidi |
| 6,892,090 B2 | 5/2005 | Verard et al. |
| 6,898,263 B2 | 5/2005 | Avinash et al. |
| 6,909,913 B2 | 6/2005 | Vining |
| 6,920,347 B2 | 7/2005 | Simon et al. |
| 6,925,200 B2 | 8/2005 | Wood et al. |
| 7,006,677 B2 | 2/2006 | Manjeshwar et al. |
| 7,072,501 B2 | 7/2006 | Wood et al. |
| 7,085,400 B1 | 8/2006 | Holsing et al. |
| 7,096,148 B2 | 8/2006 | Anderson et al. |
| 7,149,564 B2 | 12/2006 | Vining et al. |
| 7,167,180 B1 | 1/2007 | Shibolet |
| 7,174,202 B2 | 2/2007 | Bladen et al. |
| 7,179,220 B2 | 2/2007 | Kukuk |
| 7,236,558 B2 | 6/2007 | Saito et al. |
| 7,301,332 B2 | 11/2007 | Govari et al. |
| 7,315,639 B2 | 1/2008 | Kuhnigk |
| 7,324,104 B1 | 1/2008 | Bitter et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Vlegele et al. |
| 7,505,809 B2 | 3/2009 | Strommer et al. |
| 7,517,320 B2 | 4/2009 | Wibowo et al. |
| 7,518,619 B2 | 4/2009 | Stoval, III et al. |
| 7,630,752 B2 | 12/2009 | Viswanathan |
| 7,630,753 B2 | 12/2009 | Simon et al. |
| 7,659,912 B2 | 2/2010 | Akimoto et al. |
| 7,702,153 B2 | 4/2010 | Hong et al. |
| 7,751,865 B2 | 7/2010 | Jascob et al. |
| 7,756,316 B2 | 7/2010 | Odry et al. |
| 7,788,060 B2 | 8/2010 | Schneider |
| 7,792,565 B2 | 9/2010 | Vining |
| 7,805,269 B2 | 9/2010 | Glossop |
| 7,809,176 B2 | 10/2010 | Gundel |
| 7,811,294 B2 | 10/2010 | Strommer et al. |
| 7,822,461 B2 | 10/2010 | Geiger et al. |
| 7,901,348 B2 | 3/2011 | Soper et al. |
| 7,907,772 B2 | 3/2011 | Wang et al. |
| 7,929,014 B2 | 4/2011 | Akimoto et al. |
| 7,951,070 B2 | 5/2011 | Ozaki et al. |
| 7,969,142 B2 | 6/2011 | Krueger et al. |
| 7,985,187 B2 | 7/2011 | Wibowo et al. |
| 8,009,891 B2 | 8/2011 | de Vaan |
| 8,049,777 B2 | 11/2011 | Akimoto et al. |
| 8,055,323 B2 | 11/2011 | Sawyer |
| 8,102,416 B2 | 1/2012 | Ito et al. |
| 8,126,241 B2 | 2/2012 | Zarkh et al. |
| 8,131,344 B2 | 3/2012 | Strommer et al. |
| 8,170,328 B2 | 5/2012 | Masumoto et al. |
| 8,199,981 B2 | 6/2012 | Koptenko et al. |
| 8,200,314 B2 | 6/2012 | Bladen et al. |
| 8,202,213 B2 | 6/2012 | Ito et al. |
| 8,208,708 B2 | 6/2012 | Homan et al. |
| 8,219,179 B2 | 7/2012 | Ganatra et al. |
| 8,257,346 B2 | 9/2012 | Qin et al. |
| 8,267,927 B2 | 9/2012 | Dalal et al. |
| 8,290,228 B2 | 10/2012 | Cohen et al. |
| 8,298,135 B2 | 10/2012 | Ito et al. |
| 8,391,952 B2 | 3/2013 | Anderson |
| 8,417,009 B2 | 4/2013 | Mizuno |
| 8,494,612 B2 | 7/2013 | Vetter et al. |
| 8,509,877 B2 | 8/2013 | Mori et al. |
| 8,672,836 B2 | 3/2014 | Higgins et al. |
| 8,682,045 B2 | 3/2014 | Vining et al. |
| 8,696,549 B2 | 4/2014 | Holsing et al. |
| 8,698,806 B2 | 4/2014 | Kunert et al. |
| 8,700,132 B2 | 4/2014 | Ganatra et al. |
| 8,706,193 B2 | 4/2014 | Govari et al. |
| 8,709,034 B2 | 4/2014 | Keast et al. |
| 8,730,237 B2 | 5/2014 | Ruijters et al. |
| 8,768,029 B2 | 7/2014 | Helm et al. |
| 8,784,400 B2 | 7/2014 | Roschak |
| 8,798,227 B2 | 8/2014 | Tsukagoshi et al. |
| 8,798,339 B2 | 8/2014 | Mielekamp et al. |
| 8,801,601 B2 | 8/2014 | Prisco et al. |
| 8,819,591 B2 | 8/2014 | Wang et al. |
| 8,862,204 B2 | 10/2014 | Sobe et al. |
| 2002/0173783 A1 | 11/2002 | Ohno et al. |
| 2004/0249267 A1 | 12/2004 | Gilboa |
| 2005/0107679 A1 | 5/2005 | Geiger et al. |
| 2005/0182295 A1 | 8/2005 | Soper et al. |
| 2007/0293721 A1 | 12/2007 | Gilboa |
| 2008/0183073 A1 | 7/2008 | Higgins et al. |
| 2008/0240535 A1* | 10/2008 | Frangioni ............ A61B 5/0059 382/131 |
| 2009/0012390 A1 | 1/2009 | Pescatore et al. |

(56) References Cited

U.S. PATENT DOCUMENTS

| | | |
|---|---|---|
| 2009/0030306 A1 | 1/2009 | Miyoshi et al. |
| 2010/0303330 A1 | 12/2010 | Moriya |
| 2010/0310146 A1 | 12/2010 | Higgins et al. |
| 2010/0312094 A1 | 12/2010 | Guttman et al. |
| 2011/0051885 A1 | 3/2011 | Buelow et al. |
| 2011/0082363 A1 | 4/2011 | Xu et al. |
| 2011/0144432 A1 | 6/2011 | Si et al. |
| 2011/0237897 A1 | 9/2011 | Gilboa |
| 2011/0251607 A1 | 10/2011 | Kruecker et al. |
| 2012/0046928 A1 | 2/2012 | Gibbs et al. |
| 2012/0203065 A1 | 8/2012 | Higgins et al. |
| 2012/0249546 A1 | 10/2012 | Tschirren et al. |
| 2012/0280135 A1 | 11/2012 | Bal |
| 2012/0287238 A1 | 11/2012 | Onishi et al. |
| 2012/0302878 A1 | 11/2012 | Liu et al. |
| 2013/0165854 A1 | 6/2013 | Sandhu et al. |
| 2013/0223702 A1 | 8/2013 | Holsing et al. |
| 2014/0032197 A1 | 1/2014 | Kang et al. |
| 2014/0051986 A1 | 2/2014 | Zhao et al. |
| 2014/0358447 A1 | 12/2014 | Doyle et al. |

FOREIGN PATENT DOCUMENTS

| | | |
|---|---|---|
| CN | 103637845 A | 3/2014 |
| CN | 103703383 A | 4/2014 |
| EP | 2253287 A2 | 11/2010 |
| JP | 2005131319 A | 5/2005 |
| JP | 2014030659 A | 2/2014 |
| WO | 2008111070 A2 | 9/2008 |
| WO | 2011001317 A1 | 1/2011 |
| WO | 2014028394 A1 | 2/2014 |

OTHER PUBLICATIONS

Johns Hopkins. "Positron Emission Tomography (PET)". 2021 The Johns Hopkins University, The Johns Hopkins Hospital, and Johns Hopkins Health System. (Year: 2021).*

Kanick et al. "Characterization of Mediastinal Lymph Node Physiology InVivo by Optical Spectroscopy during Endoscopic Ultrasound-Guided Fine Needle Aspiration". J Thorac Oncol.2010;5: 981-987. (Year: 2010).*

Gomez et al. "Endobronchial Ultrasound for the Diagnosis and Staging of Lung Cancer". Proc Am Thorac Soc vol. 6. pp. 180-186, 2009. DOI: 10.1513/pats.200808-081LC (Year: 2009).*

International Preliminary Report on Patentability issued by the International Preliminary Examining Authority for application No. PCT/US15/38464; completed on Jun. 13, 2016 and dated Jun. 24, 2016.

Chinese Office Action for application No. 201580046881.dated Feb. 2, 2018 with English translation (16 pages).

Extended European Search Report for application No. 15815581.2 dated Feb. 20, 2018 (8 pages).

Japanese Office Action issued in Appl. No. JP 2016/575066 dated Mar. 19, 2019, together with English language translation (7 pages).

Australian Examination Report issued in Appl. No. AU2015284273 dated Mar. 5, 2019 (4 pages).

Kongkuo Lu, et al., "Extraction and visualization of the central chest lyymph-node stations", Proc. of SPIE, vol. 6915, pp. 69151B-1-69151B-15 (2008).

Jiamin Liu, et al., "Mediastinal lymph node detection and station mapping on chest CT using spatial priors and random forest", Med. Phys. vol. 43, No. 7 pp. 4362-4374 (2016).

Extended European Search Report issued in corresponding Appl. No. EP 19154836.1 dated Jul. 3, 2019 (12 pages).

Extended European Search Report issued in corresponding application 21184033.5 dated Oct. 14, 2021 (11 pages).

* cited by examiner

MAPPING DISEASE SPREAD

CROSS-REFERENCE TO RELATED APPLICATIONS

This application claims the benefit of the filing date of provisional U.S. Patent Application No. 62/624,905, filed Feb. 1, 2018, the entire contents of which are incorporated herein by reference.

BACKGROUND

Diagnosis and treatment of disease, such as cancer, in a patient's lungs require knowledge of the internal anatomy of the patient's chest. The patient's chest includes various structures and distributed networks, such as the bronchial, vascular, and lymphatic systems, and the locations of such structures as well as the patterns of flow in every patient are unique. Larger structures and lumens may be identified via analysis of radiographic images of the patient's chest. However, smaller structures may not be identifiable based on image analysis. Thus, it is hard to visualize smaller structures in a patient's chest without exploratory or interventional procedures. It is preferable to be able to diagnose the degree to which cancer has developed and spread though the patient's body without resorting to extensive interventional procedures. This process is also known as cancer staging.

For example, to determine the extent to which cancer has developed and spread through a patient's body, in the case of solid tumors, a clinician may follow the Union for International Cancer Control's (UICC) TNM staging system to determine the size and/or extent of the primary tumor, a degree of spread to the lymphatic system, and the presence of distant metastasis. The UICC's TNM staging system considers the primary tumor (T), regional lymph nodes (N), and distant metastasis (M) to describe the size and spread of cancer through the patient's body. Cancer may spread via the lymphatic or vascular systems as cancer cells break off from tumors and find their way into lymph nodes and vessels. The cancer cells may then be distributed via the lymphatic and/or vascular systems and thereby spread to other parts of the patient's body.

SUMMARY

Provided in accordance with an embodiment of this disclosure is a method for mapping a patient's lymphatic system. In an aspect of this disclosure, the method includes generating a three-dimensional (3D) model of a bronchial network and vascular network in the patient's chest based on first image data of the patient's chest, generating a lymphatic tree map by fitting a model lymph node map to the 3D model, receiving locations of a plurality of identified lymph nodes, updating the positions of lymph nodes on the lymphatic tree map by correlating the locations of the plurality of identified lymph nodes with the lymphatic tree map, and displaying the updated lymphatic tree map.

In a further aspect of the disclosure, the lymph nodes are identified based on image processing of the first image data.

In yet a further aspect of the disclosure, the plurality of lymph nodes are identified based on electromagnetic sensor (EM) data received from an EM sensor coupled to a tool being navigated about the patient's chest.

In still a further aspect of the disclosure, the lymph nodes are identified based on return signals received from a linear ultrasound scope.

In yet a further aspect of the disclosure, the lymph nodes are identified using spectroscopy.

In another aspect of the disclosure, the method further includes identifying a lesion in the 3D model.

In yet another aspect of the disclosure, the method further includes receiving second image data of the patient's chest, identifying a radiopaque element injected into a target in the second image data, and determining a distribution path from the target based on the identified radiopaque element and the updated lymphatic tree map.

In a further aspect of the disclosure, the target is a lymph node proximate the identified lesion.

In still a further aspect of the disclosure, the radiopaque element is one of radio-tagged whole blood from the patient, a collagen tracer, or a radiation tracer.

In another aspect of the disclosure, the method further includes identifying a sentinel lymph node based on the distribution path, and displaying the identified sentinel lymph node on the updated lymphatic tree map.

In yet another aspect of the disclosure, the method further includes identifying a lymph node in the distribution path a predetermined distance from the sentinel lymph node, and displaying the identified lymph node on the updated lymphatic tree map.

In a further aspect of the disclosure, the predetermined distance is at least about 5 cm.

In yet a further aspect of the disclosure, the predetermined distance is between about 7 cm and about 10 cm.

In still a further aspect of the disclosure, the identified lymph node is a lymph node with at least three other lymph nodes between the identified lymph node and the sentinel lymph node.

In another aspect of the disclosure, the method further includes determining areas to which spread may occur based on the identified sentinel lymph node and the distribution path, and displaying the areas to which spread may occur on the updated lymphatic tree map.

In a further aspect of the disclosure, the model lymph node map is the International Association for the Study of Lung Cancer (IASLC) lymph node map.

Provided in accordance with an embodiment of the disclosure is a method for mapping a patient's vascular system. In an aspect of the disclosure, the method includes generating a three-dimensional (3D) model of a bronchial network in the patient's chest based on image data of the patient's chest, generating a vascular tree map by fitting a model vascular map to the 3D model, receiving locations of a plurality of identified vascular structures, updating the positions of vascular structures on the vascular tree map by correlating the locations of the plurality of identified vascular structures with the vascular tree map, and displaying the updated vascular tree map.

In a further aspect of the disclosure, the plurality of vascular structures are identified based on electromagnetic sensor (EM) data received from an EM sensor coupled to a tool being navigated about the patient's chest.

Provided in accordance with an embodiment of the disclosure is a method for mapping a patient's lymphatic system. In an aspect of the disclosure, the method includes receiving image data of a patient's chest, generating a three-dimensional (3D) model of a bronchial network based on the received image data, generating a lymphatic tree map by fitting a model lymph node map to the generated 3D model, receiving locations of a plurality of identified lymph nodes based on electromagnetic sensor (EM) data received from an EM sensor coupled to a tool being navigated about the patient's chest, and updating the positions of lymph nodes on the lymphatic tree map based on the locations of the plurality of identified lymph nodes.

In a further aspect of the disclosure, the method further includes displaying the updated lymphatic tree map.

Any of the above aspects and embodiments of the disclosure may be combined without departing from the scope of this disclosure.

BRIEF DESCRIPTION OF THE DRAWINGS

Various aspects and features of this disclosure are described hereinbelow with references to the drawings, wherein.

DETAILED DESCRIPTION

Current methodologies for locating and identifying lymph nodes, lymphatic networks, and vascular networks, as well as their relationships to one another, often rely primarily on the abilities of the clinician. Improvements in systems and methods to aid the clinician in identifying and mapping locations of lymph nodes, lymphatic networks, and vascular networks, as well as their relationships to one another, are desired.

This disclosure relates to systems and methods for mapping a patient's lymphatic and vascular systems, and predicting spread of disease based on distribution patterns of, and interrelation between, the patient's lymphatic and vascular systems and the target area itself. More particularly, the disclosure relates to fitting a model lymphatic tree map and/or model vascular tree map to a model of the patient's bronchial network, updating the map with the actual locations of the patient's lymph nodes and/or vascular structures, identifying one or more sentinel lymph nodes and/or vascular structures which may form distribution paths by which disease may spread from a lesion, and predicting where disease is most likely to spread based on the identified sentinel lymph nodes and/or vascular structures. Pre-procedural imaging of the patient's chest may be performed to create a visual representation, such as a three-dimensional (3D) model of a patient's chest, including lumens such as the bronchial, vascular, and lymphatic trees, pleural surfaces and fissures of the patient's lungs, and/or tumors or other aberrant structures that may be present in the patient's lungs. The 3D model may be generated using one or more software applications executing on a computer. The application may, for example, generate the 3D model or map of the patient's chest based on radiographically obtained images, such as computed tomography (CT) images, magnetic resonance imaging (MRI) images, positron emission tomography (PET) images, X-ray images, cone-beam computed tomography (CBCT) images, and/or fluoroscopic images, as well as ultrasound images, and/or any other applicable imaging modality. The images may be processed to create a volume of image data of the patient's chest based upon which the 3D model is generated. The image data and/or 3D model may further be processed to identify one or more targets, such as tumors, lesions, or other aberrant structures, in the patient's chest. For example, the application may identify the locations of lumens, such as airways, blood vessels, and/or lymphatic structures from the CT image data, and further determine the locations of one or more diagnostic or treatment targets (referred to hereinafter as "targets").

The application may then receive or load a model lymph node map, such as the International Association for the Study of Lung Cancer (IASLC) map, which includes the locations of lymph nodes in a model patient's body. Thereafter, the application may fit the model lymph node map to the 3D model to align the model map with the real patient's body and the identified structures in the patient's chest. A lymphatic tree map of the patient's lymphatic system may then be generated based on the model lymph node map fitted to the 3D model. The generated lymphatic tree map may further be fitted and/or updated based on known locations of lymph nodes in the patient's chest. For example, the lymphatic tree map may be updated based on locations of lymph nodes identified based on the image data and/or based on location data of tools used to sample, such as via biopsy, lymph nodes in the patient's body.

The 3D model, radiographic image data, and lymphatic tree map may then be displayed to and viewed by a clinician and/or surgeon to plan a medical procedure, such as a diagnostic or treatment procedure, including biopsy, ablation, radiation, and/or surgical or interventional procedure. For example, the clinician may review the 3D model, radiographic image data, and/or lymphatic tree map to identify a lesion or other target for diagnosis and/or treatment. The application may then determine a path to the lesion or target, as further described below. The 3D model, lymphatic tree map, and/or procedure plan may further be stored for later viewing during the medical procedure in an operating room or the like.

Additionally, the application may receive, load, or generate a vascular tree map of the patient's vascular system. In some embodiments, a model vascular tree map of vascular structures in a model patient's body may be fitted to the 3D model to align the model vascular tree map with the real patient's body. A vascular tree map of the patient's vascular system may then be generated based on the model vascular tree map fitted to the 3D model. Additionally or alternatively, the application may process the radiographic image data and/or 3D model to identify vascular structures in the patient's body and generate the vascular tree map based on such identified vascular structures.

During the medical procedure, the 3D model, vascular tree map, and/or lymphatic tree map may be displayed, as further described below, to assist the clinician in navigating one or more tools to one or more targets. For example, the clinician may biopsy a lesion and/or lymph node to obtain a tissue sample which may be analyzed to determine if cancer cells are present. A radiopaque element, such as a dye, tracer, or radio-tagged fluid, or other elements such as radioisotopes, etc., may be injected into a lesion or target to identify distribution and/or drainage paths from the lesion or target.

After the radiopaque element has been injected into one or more lesions or targets, additional image data may be acquired to identify the distribution and/or drainage paths from the lesions or targets. For example, the application may process the additional image data to identify lymphatic lumens and nodes as well as blood vessels via which the radiopaque element has drained after injection. The application may then identify, based on the distribution and/or drainage paths, one or more sentinel lymph nodes, and predicted disease spread from the lesion or target, as well as vascular ingress and egress from the target and/or area surrounding the target.

The methods, systems, apparatus, and computer-readable media described herein are useful in various planning and/or navigation contexts for diagnostic and/or treatment procedures performed in the patient's chest. For example, in an embodiment in which a clinician is performing diagnosis of lesions in an area of the patient's lungs, the methods and systems may provide the clinician with various views of the patient's lungs and the bronchial, vascular, and lymphatic trees therein. Additionally, as will be described in further detail below, the methods and systems may provide the clinician with the ability view distribution/drainage paths from the lesions via the lymphatic and vascular systems to predict spread of disease. These and other aspects of this disclosure are detailed hereinbelow.

Methods for planning and performing diagnosis and/or treatment in a patient's chest may be implemented via an electromagnetic navigation (EMN) system. Generally, in an embodiment, the EMN system may be used in planning diagnosis and/or treatment of an area of the patient's chest by identifying the locations of one or more targets in the patient's chest, selecting one or more of the targets as a target location, determining a pathway to the target location, navigating a positioning assembly to the target location, and navigating a variety of tools to the target location. Once at the target location, the EMN system may be used to aid the clinician in placing one or more tools at the target location and performing one or more diagnostic and/or treatment functions at the target location. The EMN system may be configured to display various views of the patient's body, and of the aforementioned 3D model, lymphatic tree map, and/or vascular tree map.

Figure 1:
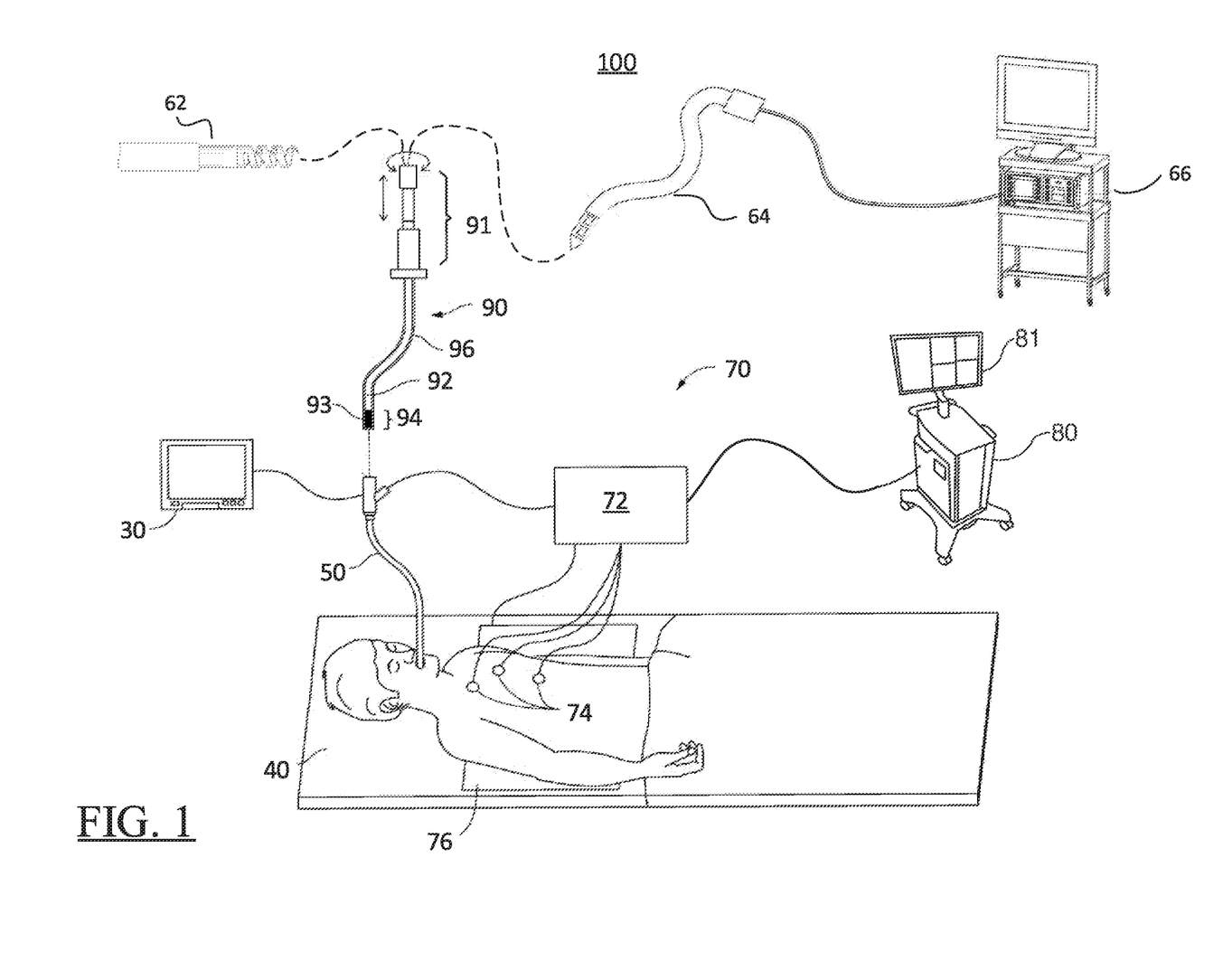
FIG. 1 is a schematic diagram of a system for planning and performing treatment of an area of a patient's chest endobronchially, according to an embodiment of the disclosure.

FIG. 1 illustrates an EMN system 100 suitable for implementing methods for performing endobronchial diagnostic and/or treatment procedures in an area of a patient's chest is provided in accordance with this disclosure. One such EMN system 100 is the ELECTROMAGNETIC NAVIGATION BRONCHOSCOPY® system currently sold by Covidien LP, a division of Medtronic PLC. As shown in FIG. 1, EMN system 100 is used to perform one or more treatment procedures on a patient supported on an operating table 40. In this regard, EMN system 100 generally includes a bronchoscope 50, monitoring equipment 30, an electromagnetic (EM) tracking system 70, and a computing device 80.

Bronchoscope 50 is configured for insertion through the patient's mouth and/or nose into the patient's airways. Bronchoscope 50 includes a source of illumination and a video imaging system (not explicitly shown) and is coupled to monitoring equipment 30, for example, a video display, for displaying the video images received from the video imaging system of bronchoscope 50. In an embodiment, bronchoscope 50 may operate in conjunction with a catheter guide assembly 90. Catheter guide assembly 90 includes a locatable guide (LG) 92 and an extended working channel (EWC) 96 configured for insertion through a working channel of bronchoscope 50 into the patient's airways (although the catheter guide assembly 90 may alternatively be used without bronchoscope 50). Catheter guide assembly 90 includes a handle 91 connected to EWC 96, and which can be manipulated by rotation and compression to steer LG 92 and EWC 96. EWC 96 is sized for placement into the working channel of bronchoscope 50. In the operation of catheter guide assembly 90, LG 92, including an EM sensor 94, is inserted into EWC 96 and locked into position such that EM sensor 94 extends a desired distance beyond a distal tip 93 of EWC 96. The location of EM sensor 94, and thus distal tip 93 of EWC 96, within an EM field generated by EM field generator 76, can be derived by tracking module 72 and computing device 80. For a more detailed description of catheter guide assembly 90, reference is made to commonly-owned U.S. Pat. No. 9,247,992, entitled "MICROWAVE ABLATION CATHETER AND METHOD OF UTILIZING THE SAME", filed on Mar. 15, 2013, by Ladtkow et al., the entire contents of which are hereby incorporated by reference.

LG 92 and EWC 96 are selectively lockable relative to one another via a locking mechanism 99. A six degrees-of-freedom EM tracking system 70, e.g., similar to those disclosed in U.S. Pat. No. 6,188,355 and published PCT Application Nos. WO 00/10456 and WO 01/67035, entitled "WIRELESS SIX-DEGREE-OF-FREEDOM LOCATOR", filed on Dec. 14, 1998 by Gilboa, the entire contents of each of which is incorporated herein by reference, or any other suitable positioning measuring system, is utilized for performing navigation, although other configurations are also contemplated.

EM tracking system 70 may be configured for use with catheter guide assembly 90 to track a position of EM sensor 94 as it moves in conjunction with EWC 96 through the airways of the patient, as detailed below. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The six degrees of freedom coordinates of reference sensors 74 are sent as data to computing device 80, which includes application 81, where the data from sensors 74 are used to calculate a patient coordinate frame of reference.

Although EM sensor 94 is described above as being included in LG 92 it is also envisioned that EM sensor 94 may be embedded or incorporated within a treatment tool, such as a biopsy tool 62 and/or an ablation tool 64, or a diagnostic tool, such as camera tool, light sensor, linear ultrasound tool, etc., where the treatment tool may alternatively be utilized for navigation without need of LG 92 or the necessary tool exchanges that use of LG 92 requires. EM sensor 94 may also be embedded or incorporated within EWC 96, such as at a distal portion of EWC 96, thereby enabling tracking of the distal portion of EWC 96 without the need for a separate LG 92. According to an embodiment, treatment tools 62, 64 are configured to be insertable into catheter guide assembly 90 following navigation to a target location and removal of LG 92. Biopsy tool 62 may be used to collect one or more tissue sample from the target location, and in an embodiment, is further configured for use in conjunction with tracking system 70 to facilitate navigation of biopsy tool 62 to the target location, and tracking of a location of biopsy tool 62 as it is manipulated relative to the target location to obtain the tissue sample. Ablation tool 64 is configured to be operated with a generator 66, such as a radio frequency generator or a microwave generator, and may include any of a variety of ablation tools and/or catheters, examples of which are more fully described in U.S. Pat. Nos. 9,259,269; 9,247,993; 9,044,254; and 9,370,398, and U.S. Patent Application Publication No. 2014/0046211, all entitled "MICROWAVE ABLATION CATHETER AND METHOD OF USING THE SAME", filed on Mar. 15, 2013, by Ladtkow et al., the entire contents of each of which is incorporated herein by reference. Though shown as a biopsy tool and microwave ablation tool in FIG. 1, those of skill in the art will recognize that other tools including for example RF ablation tools, brachytherapy tools, endobronchial ultrasound devices, and others may be similarly deployed and tracked without departing from the scope of this disclosure.

Computing device 80 includes hardware and/or software, such as an application 81, used to facilitate the various phases of an EMN procedure, including generating the 3D model, generating the lymphatic tree map, identifying a target location, planning a pathway to the target location, registering the 3D model with the patient's actual airways, and navigating to the target location. Application 81 may further be used to process image data to determine distribution/drainage paths from a lesion and predict spread of disease, as further described below. For example, computing device 80 utilizes data acquired from a CT scan, cone beam computed tomography (CBCT) scan, magnetic resonance imaging (MRI) scan, positron emission tomography (PET) scan, ultrasound scan, X-ray scan, and/or any other suitable imaging modality to generate and display the 3D model of the patient's airways, to enable identification of a target location on the 3D model (automatically, semi-automatically or manually), and allow for the determination and selection of a pathway through the patient's airways to the target location. While the CT scan image data may have gaps, omissions, and/or other imperfections included in the image data, the 3D model is a smooth representation of the patient's airways, with any such gaps, omissions, and/or imperfections in the CT scan image data filled in or corrected. The 3D model may be presented on a display monitor associated with computing device 80, or in any other suitable fashion. An example of the planning software described herein can be found in U.S. Patent Application Publication Nos. 2014/0281961, 2014/0270441, and 2014/0282216, filed by Baker et al. on Mar. 15, 2013, and entitled "PATHWAY PLANNING SYSTEM AND METHOD", the contents of all of which are incorporated herein by reference. Further examples of the planning software can be found in commonly assigned U.S. Patent Application Publication No. 2016/0000302, entitled "SYSTEM AND METHOD FOR NAVIGATING WITHIN THE LUNG", filed on Jun. 29, 2015, by Brown et al., the contents of which are incorporated herein by reference.

Using computing device 80, various views of the 3D model and/or lymphatic tree map may be displayed to and manipulated by a clinician to facilitate identification of a target location. As noted above, the target location may be a surgical site where treatment is to be performed, and/or a portion of, entire lobe, or multiple lobes of the patient's lungs requiring treatment. The 3D model may include, among other things, a model airway tree corresponding to the actual airways of the patient's lungs, and show the various passages, branches, and bifurcations of the patient's actual airway tree. Additionally, the 3D model may include lesions, markers, blood vessels and vascular structures, organs, other physiological structures, and/or a 3D rendering of the pleural surfaces and fissures of the patient's lungs. Some or all of the aforementioned elements may be selectively displayed, such that the clinician may choose which elements should be displayed when viewing the 3D model. Additionally, the lymphatic tree map may be displayed as part of the 3D model or as a separate map which may be overlaid onto the 3D model.

During a procedure, EM sensor 94, in conjunction with tracking system 70, enables tracking of EM sensor 94 (and thus distal tip 93 of EWC 96 or tools 62, 64) as EM sensor 94 is advanced through the patient's airways following the pathway planned during the planning phase. As an initial step of the procedure, the 3D model is registered with the patient's actual airways. One potential method of registration involves navigating LG 92 into each lobe of the patient's lungs to at least the second bifurcation of the airways of that lobe. The position of LG 92 is tracked during this registration phase, and the 3D model is iteratively updated based on the tracked position of the locatable guide within the actual airways of the patient's lungs. This registration process is described in commonly-owned U.S. Patent Application Publication No. 2011/0085720, entitled "AUTOMATIC REGISTRATION TECHNIQUE," filed on May 14, 2010, by Barak et al., and U.S. Patent Publication No. 2016/0000356, entitled "REAL-TIME AUTOMATIC REGISTRATION FEEDBACK", filed on Jul. 2, 2015, by Brown et al., the contents of each of which are incorporated herein by reference. While the registration process focuses on aligning the patient's actual airways with the airways of the 3D model, registration also ensures that the position of vascular structures, pleural surfaces, and fissures of the lungs are accurately determined.

At various times during the procedure, the clinician may cause additional scans to be performed on the patient. These additional scans may be used to determine distribution/drainage paths from a lesion and/or lymph node by identifying drainage, via the lymphatic and/or vascular systems, of a radiopaque element that has been injected into the lesion and/or lymph node. As such, the additional scans may be fluoroscopic scans, but those skilled in the art will recognize that other imaging modalities may also be used. For example, CBCT imaging, C-arm x-ray imaging, and/or any other applicable imaging modality may also be used without departing from the scope of this disclosure. The additional scans may be directed at a particular location in the patient's chest where the lesion and/or lymph node that has been injected with the radiopaque element is located. Application 81 may receive the image data acquired by the additional scans and process the image data to identify the radiopaque element and determine distribution paths from the lesion and/or lymph node based on the drainage of the radiopaque element.

Application 81 may then update and/or enhance the lymphatic tree map and/or vascular tree map based on the additional image data, and particularly, the determined distribution paths. Application 81 may further identify lymphatic and/or vascular structures in the additional image data and update and/or enhance the lymphatic tree map and/or vascular tree map based on the identified lymphatic and/or vascular structures that are in different locations and/or not previously included in the lymphatic tree map and/or vascular tree map. For example, the additional image data may provide a clearer image of the particular part of the patient's body that was imaged by the additional scan than by the original scan, and application 81 may update and/or enhance a portion of the lymphatic tree map and/or vascular tree map based on the additional image data. Application 81 may then display the updated lymphatic tree map and/or vascular tree map showing the determined distribution paths.

After determining the distribution paths, application 81 may determine, based on the distribution paths, a type of disease being diagnosed and/or treated, and/or input from the clinician, one or more lymph nodes from which to obtain a biopsy sample to determine if the disease has spread to such lymph nodes. Additionally or alternatively, in the case of surgery, application 81 may determine whether it is necessary to remove a portion of tissue from the patient's body. Application 81 may then generate a plan for obtaining the biopsy samples, similar to the navigation plan described above.

Figure 2:
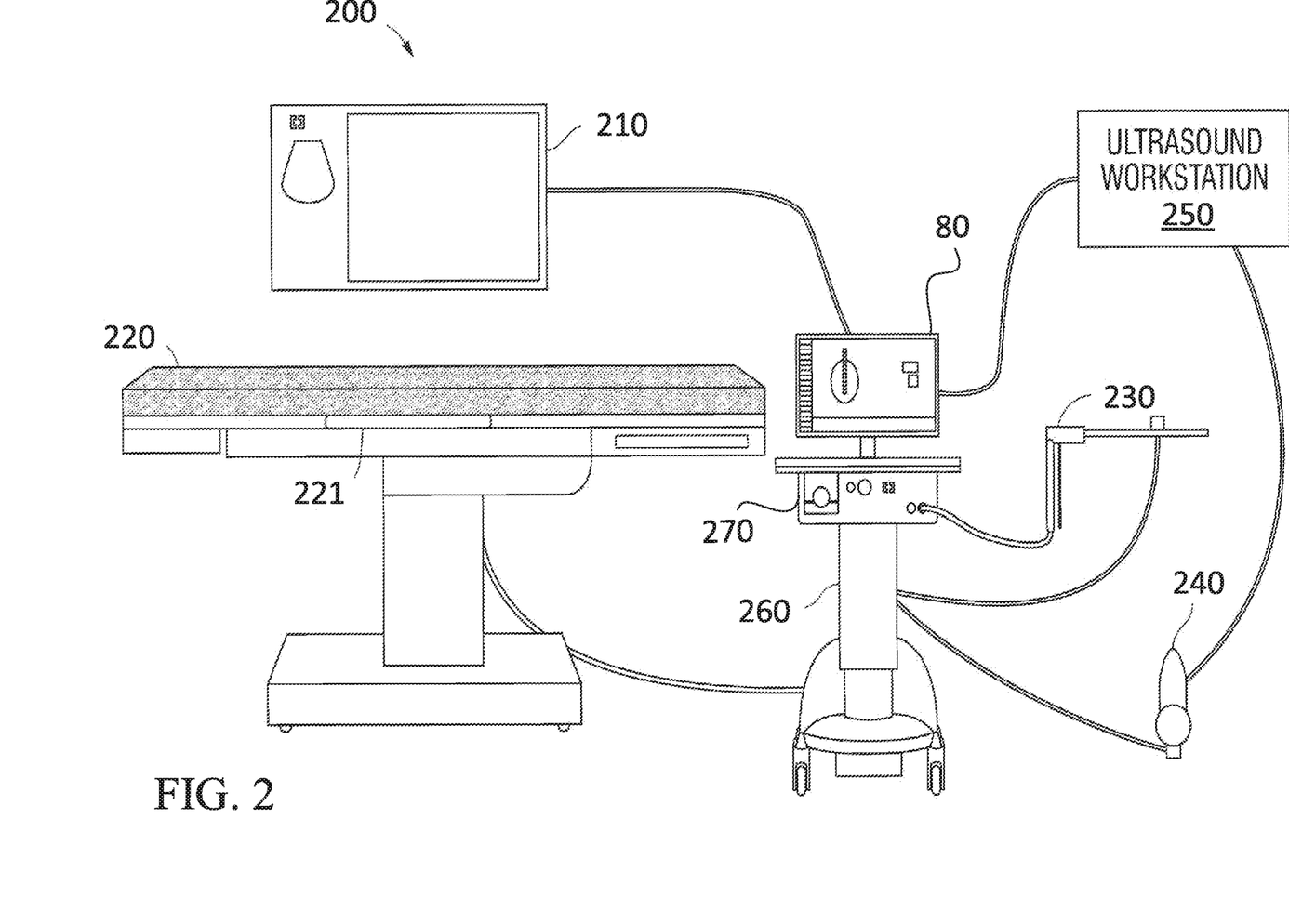
FIG. 2 is a schematic diagram of a system for planning and performing treatment of an area of a patient's chest percutaneously and/or laparoscopically, according to an embodiment of the disclosure.

Turning now to FIG. 2, there is shown a system 200 suitable for implementing methods for performing percutaneous and/or laparoscopic diagnostic and/or treatment procedures in an area of a patient's chest, in accordance with embodiments of this disclosure. System 200 includes a display 210, a table 220 including an electromagnetic (EM) field generator 221, a tool 230, an ultrasound sensor 240 connected to an ultrasound workstation 250, a peristaltic pump 260, and a computing device 80 attached to or in operable communication with a microwave generator 270. Computing device 80 may be similar to the computing device 80 described above with reference to FIG. 1. In addition, computing device 80 may be configured to control microwave generator 270, peristaltic pump 260, a power supply (not shown), and/or any other accessories and peripheral devices relating to, or forming part of, system 200. Display 210 is configured to output instructions, images, and messages relating to the performance of the medical procedure.

Table 220 may be, for example, an operating table or other table suitable for use during a medical procedure, which includes EM field generator 221. EM field generator 221 is used to generate an EM field during the medical procedure and forms part of an EM tracking system that is used to track the positions of tools within the patient's chest. EM field generator 221 may include various components, such as a specially designed pad to be placed under, or integrated into, an operating table or patient bed. An example of such an EM tracking system is the AURORA™ system sold by Northern Digital Inc.

Tool 230 is a medical instrument for accessing and performing diagnostic and/or treatment procedures at a target location. For example, tool 230 may be biopsy needle used to obtain a tissue sample from a target location in the patient's chest. In another example, tool 230 may be an ablation antenna, such as an RF or microwave ablation antenna, used to ablate the target location in the patient's chest. In yet another embodiment, tool 230 may include a camera, such as a laparoscope, ultrasound probe, or other device for capturing images (whether optical or radiographic) inside the patient's body. In some embodiments, tool 230 is a percutaneous tool insertable through the patient's skin to access one or more target locations. In other embodiments, tool 230 is a laparoscopic tool insertable into the patient's body via a laparoscopic port or trocar. Multiple tools may be used simultaneously, and in the case of laparoscopic tools, multiple laparoscopic ports or trocars may be used simultaneously. In various embodiments, tool 230 may be a robotic tool associated with a robotic surgical system, or a manual tool operated by the clinician. Tool 230 may include, or have attached to it, and EM sensor enabling the EM tracking system to track the location, position, and orientation (also known as the "pose") of tool 230 inside the patient's chest. If tool 230 is a microwave ablation antenna, microwave generator 270 may be configured to output microwave energy to tool 230. Peristaltic pump 260 may be configured to pump fluid through tool 230 to cool tool 230. While this disclosure describes the use of system 200 in a surgical environment, it is also envisioned that some or all of the components of system 200 may be used in alternative settings, for example, an imaging laboratory and/or an office setting.

In addition to the EM tracking system, the above-described instruments, including tool 230, may also be visualized by using ultrasound imaging. Ultrasound sensor 240, such as an ultrasound wand, may be used to image one or more portions of the patient's chest during the medical procedure to visualize the location of the instruments, such as tool 230, inside the patient's chest, for example, to confirm the position and/or placement of tool 230. Ultrasound sensor 240 may have an EM tracking sensor embedded within or attached to the ultrasound wand, for example, a clip-on sensor or a sticker sensor. Ultrasound sensor 240 may be positioned in relation to tool 230 such that tool 230 is at an angle to the ultrasound image plane, thereby enabling the clinician to visualize the spatial relationship of tool 230 with the ultrasound image plane and with objects being imaged. Further, the EM tracking system may also track the location of ultrasound sensor 240. In some embodiments, one or more ultrasound sensors 240 may be placed inside the patient's body. The EM tracking system may then track the location of such ultrasound sensors 240 and tool 230 inside the patient's body. Ultrasound workstation 250 may be used to configure, operate, and/or view images captured by ultrasound sensor 240. Likewise, computing device 80 may be used to configure, operate, and/or view images captured by ultrasound sensor 240, either directly or relayed via ultrasound workstation 250.

Various other instruments or tools, such as LIGASURE® devices, surgical staplers, etc. available from Covidien LP, a division of Medtronic PLC, may also be used during the performance of the medical procedure. In embodiments where tool 230 is a microwave ablation probe, the microwave ablation probe may be used to ablate a lesion or tumor at a target location by using microwave energy to heat tissue in order to denature or kill cancerous cells. The construction and use of a system including such an ablation probe is more fully described in co-pending U.S. Patent Application Publication No. 2016/0058507, entitled MICROWAVE ABLATION SYSTEM, filed on Aug. 26, 2014, by Dickhans, U.S. Pat. No. 9,247,992, entitled MICROWAVE ABLATION CATHETER AND METHOD OF UTILIZING THE SAME, filed on Mar. 15, 2013, by Ladtkow et al., and U.S. Pat. No. 9,119,650, entitled MICROWAVE ENERGY-DELIVERY DEVICE AND SYSTEM, filed on Mar. 15, 2013, by Brannan et al., the entire contents of each of which are hereby incorporated by reference.

As noted above, the location of tool 230 within the patient's chest may be tracked during the medical procedure. An example method of tracking the location of tool 230 is by using the EM tracking system, which tracks the location of tool 230 by tracking sensors attached to or incorporated in tool 230. Various types of sensors may be used, such as a printed sensor, the construction and use of which is more fully described in co-pending U.S. Patent Application Publication No. US 2016/017487314/919,950, entitled "MEDICAL INSTRUMENT WITH SENSOR FOR USE IN A SYSTEM AND METHOD FOR ELECTROMAGNETIC NAVIGATION", filed Oct. 22, 2015, by Greenburg et al., the entire contents of which are incorporated herein by reference. A percutaneous treatment system similar to the above-described system 200 is further described in co-pending U.S. Patent Application Publication No. 2016/0317224, entitled "MICROWAVE ABLATION PLANNING AND PROCE- DURE SYSTEMS", filed on Apr. 15, 2016, by Girotto et al., the entire contents of which are incorporated herein by reference.

While the above-described system 200 uses a microwave generator 270 to provide microwave energy to tool 230, those skilled in the art will appreciate that various other types of generators and tools may be used without departing from the scope of this disclosure. For example, radio frequency (RF) ablation tools receiving RF energy from RF generators may be substituted for the microwave generators and ablation tools described above.

Figure 3A:
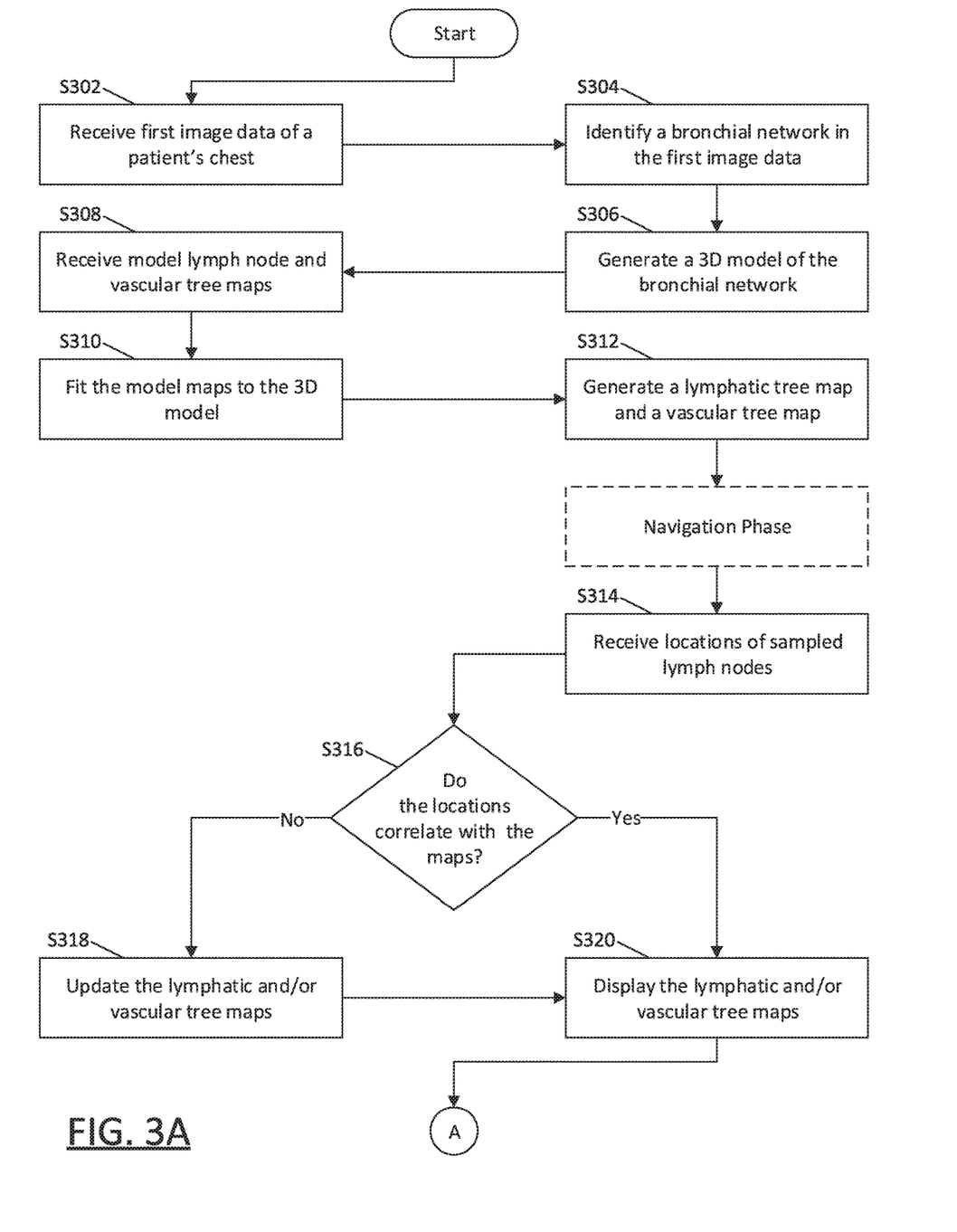
FIGS. 3A and 3B show a flowchart of an example method for predicting spread of disease based on a lymphatic tree map, according to an embodiment of the disclosure.
Figure 3B:
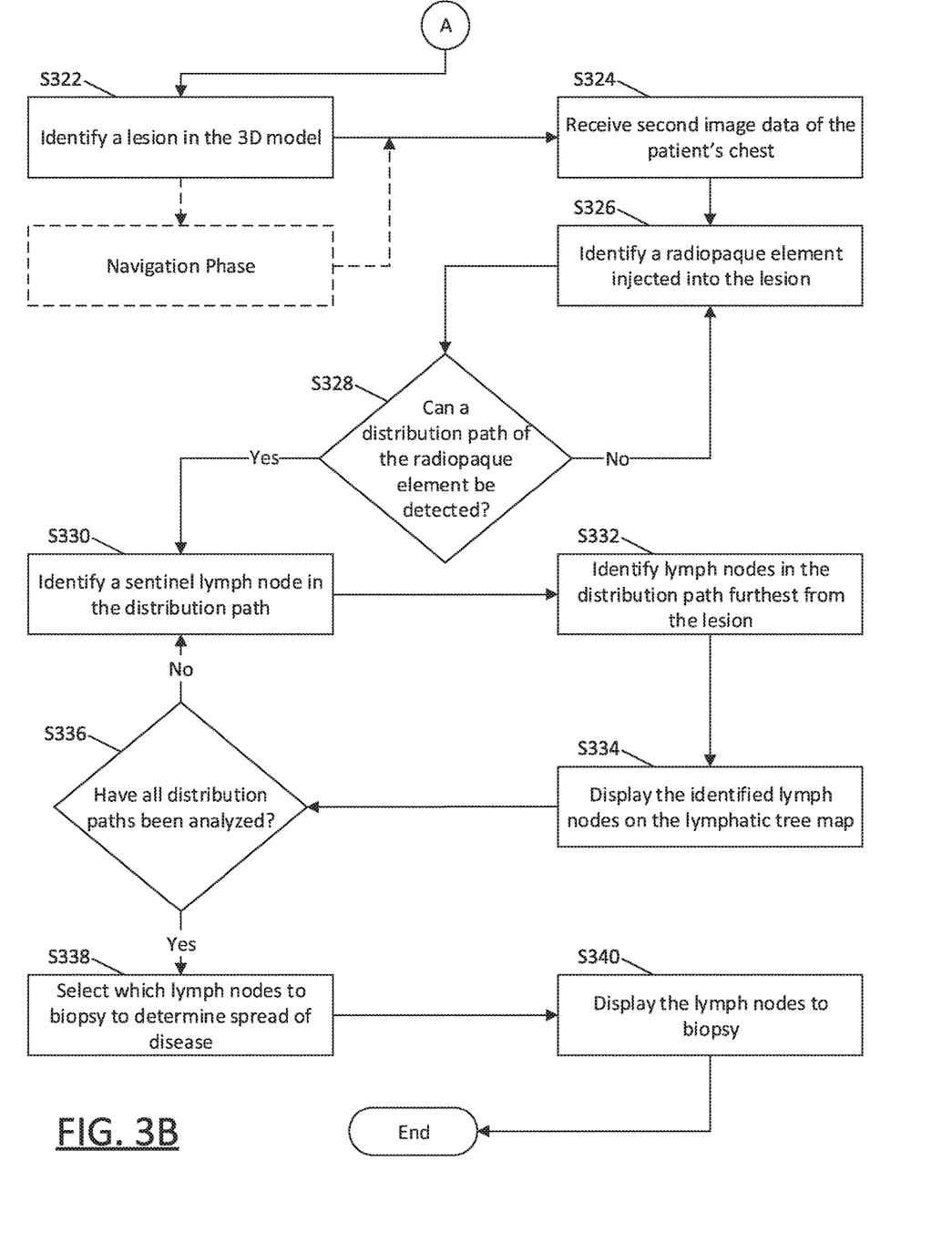

Turning now to FIG. 3, there is shown a flowchart of an illustrative method of performing diagnosis and/or treatment of an area of a patient's lungs, in accordance with an embodiment of this disclosure. Starting at step S302, computing device 80 receives image data of the patient's lungs. In some embodiments, image data from multiple pre-operative scans may be used in combination. In other embodiments, only image data from a most recent scan may be used. The image data may be received in, or converted to, a uniform data format, such as the digital imaging and communications in medicine (DICOM) standard. To distinguish the image data received at step S302 from image data received during additional scans performed at various times during the medical procedure, as described below, the image data received at step S302 will hereinafter be referred to as "first image data."

Next, at step S304, application 81 processes the first image data to identify an organ in the patient's body in the first image data. For example, application 81 may identify the patient's lungs, and particularly, the bronchial network of the patient's airways in the first image data. The image processing may include automatic and/or user-assisted image analysis to identify the patient's lungs in the first image data. Various image processing methods may be used, including region growing techniques, as described in co-pending U.S. Patent Application Publication No. 2016/0038248, entitled "TREATMENT PROCEDURE PLANNING SYSTEM AND METHOD", filed on Aug. 10, 2015, by Bharadwaj et al., and co-pending U.S. Patent Application Publication No. 2016/0005193, entitled "SYSTEM AND METHOD FOR SEGMENTATION OF LUNG", filed on Jun. 30, 2015, by Markov et al., the contents of each of which are incorporated herein by reference. Application 81 may further determine the locations of other structures, such as arteries and veins of the patient's vascular tree, and/or lymphatic lumens and nodes of the patient's lymphatic tree.

Thereafter, at step S306, application 81 generates a three-dimensional (3D) model of the patient's lungs. The 3D model includes graphical representations of the patient's lungs, showing the locations of the lumens and structures of the bronchial, vascular, and lymphatic trees, as well as the pleural surfaces and fissures of the patient's lungs, and/or tumors or other aberrant structures that may be present in the patient's lungs, as was identified in step S304. Next, at step S308, application 81 receives or loads a model lymph node map and/or a model vascular tree map. The model lymph node map may be a map showing the locations of lymph nodes in a model patient's body, and the model vascular tree map may be a map showing the locations of vascular structures in a model patient's body. An example of such a model lymph node map is the International Association for the Study of Lung Cancer's (IASLC) lymph node map. However, other model lymph node maps and model vascular tree maps may also be used and/or generated based on data collected from the patient and/or other patients with similar body types.

At step S310, the model lymph node map and/or model vascular tree map is fitted to the 3D model. For example, the model lymph node map and/or model vascular tree map may be overlaid onto the 3D model and adjusted to fit the contours and locations of structures in the 3D model. For example, the model lymph node map and/or model vascular tree map may scaled to fit various anchor points, such as the structures identified in step S304, and/or may be tethered to various contours of the patient's body as reflected in the 3D model.

Application 81 then, at step S312, generates a lymphatic tree map and/or vascular tree map based on the model lymph node map and/or model vascular tree map as fitted to the 3D model. The lymphatic tree map and/or vascular tree map may be separate maps from the 3D model and/or may be selectively displayable layers of the 3D model. Thus, the lymphatic tree map will be a map of the expected locations of lymph nodes fitted to the patient's body based on the 3D model, and the vascular tree map will be a map of the known locations of vascular structures fitted to the patient's body based on the 3D model.

In some embodiments, following step S312, a navigation phase, as described above, may commence. The navigation phase may include the endobronchial navigation of LG 92 and/or tool 62 of system 100 to a target location in the patient's chest to obtain a biopsy at the target location. Alternatively, the navigation phase may include the percutaneous and/or laparoscopic insertion into the patient's chest and navigation of tool 230 to the target location. In some embodiments, a navigation phase may not be necessary to identify the locations of lymph nodes, because predictive models can be generated such that, based on the position and interaction of the target location and the lymphatic and vascular networks, a number of suggested locations of where to obtain tissue samples may be identified before an exploratory navigation or treatment is performed. During the navigation phase, various tools may be navigated about the patient's chest to identify one or more lesions and/or lymph nodes. For example, after reviewing the 3D model, vascular tree map, and/or lymphatic tree map, the clinician may identify a lesion or area of interest in the patient's lungs. The clinician may then navigate one or more of the tools described above to the lesion or area of interest in the patient's lungs. When the tool has been navigated proximate a lesion or area of interest, the position of the tool may be marked on the 3D model as a location of the lesion or area of interest. The tool may then further be navigated to detect the presence and locations of lymph nodes and/or vascular structures proximate the lesion or area of interest. For example, various camera tools, light sensors, and/or linear ultrasound scopes may be navigated about the patient's chest to detect the presence and locations of lesions, vascular structures, and/or lymph nodes. In addition to detecting the presence and locations of lesions, vascular structures, and/or lymph nodes, one or more tissue samples may also be obtained from biopsies of the lesions and/or lymph nodes during the navigation phase. In other embodiments, the navigation phase does not commence immediately following step S312, and instead commences after step S322, described below.

Regardless, at step S314, application 81 receives locations of identified lymph nodes and/or vascular structures. The locations may be based on the detected locations of lymph nodes and/or vascular structures via the use of tools if a navigation phase commenced after step S312, as described above. For example, an ultrasound imaging tool may be used during the navigation phase to acquire image data of various structures about and/or proximate the target location. Additionally, various surgical approaches, including mediastinoscopy, video-assisted thoracic surgery (VATS), Chamberlain procedure, etc., may be undertaken to identify lymph nodes and/or vascular structures about and/or proximate the target location. Alternatively, or in addition, the locations may be based on locations of lymph nodes and/or vascular structures marked and stored during prior procedures. Further still, the locations may be based on the image processing performed at step S304 and/or additional image processing performed thereafter, whether on the first image data received at step S302 or on additional image data received at step S314, to identify locations of lymph nodes and/or vascular structures in the first image data. For example, one or more scans, such as MRI scans, PET scans, gallium scans, ultrasound scans, etc., may be performed and the image data from such scans received and processed by computing device 80 at step S314 to identify the locations of lymph nodes and/or vascular structures. As such, lymph nodes and vascular structures outside of the patient's chest may also be identified at step S314 and included in the lymphatic tree map and/or vascular tree map, respectively.

Thereafter, at step S316, application 81 compares the locations of lymph nodes and vascular structures received at step S314 to the lymphatic tree map and vascular tree map, respectively, as generated at step S312, to determine whether the received locations of lymph nodes and vascular structures correlate with the lymphatic tree map and/or vascular tree map, respectively. If the received locations of lymph nodes and/or vascular structures do not correlate with the lymphatic tree map and/or vascular tree map, application 81 updates the lymphatic tree map and/or vascular tree map at step S318. For example, locations of lymph nodes and/or vascular structures detected during navigation and/or identified in the first image data received at step S302 and/or the additional image data received at step S314 may be compared with locations of lymph nodes and/or vascular structures in the lymphatic tree map and/or vascular tree map, respectively, and the lymphatic tree map and/or vascular tree map may be updated and/or adjusted based on the detected and/or identified locations of lymph nodes and/or vascular structures. Additionally, for lymph nodes or other structures of which tissue samples were obtained during a navigation phase following step S312, or prior to the start of the current procedure, and results of analysis of such tissue samples are available, the lymphatic tree map, vascular tree map, and/or 3D model may further be updated to reflect the results of such analysis. For example, if a tissue sample obtained from a lymph node tests positive for the presence of cancer cells, such a lymph node may be displayed in a different manner and/or different color in the lymphatic tree map to identify the lymph node as testing positive for cancer.

Thereafter, or if the received locations match the lymphatic tree map and/or vascular tree map (and thus no updating is necessary) application 81 displays the lymphatic tree map and/or vascular tree map, such as on a display 506, described below with reference to FIG. 5, at step S320. Application 81 may also display the 3D model. As noted above, the lymphatic tree map and/or vascular tree map may be separate maps displayed in conjunction with the 3D model, and/or be selectively displayable layers of the 3D model.

Application 81 may then, at step S322, identify one or more lesions and/or tumors in the 3D model. The identification may be based on input received from the clinician and/or image analysis of the first image data received at step S302 and/or the additional image data received at step S314. In embodiments, application 81 may highlight (or in some other way display) one or more areas as potential lesions and/or tumors detected via image analysis of the image data for review by the clinician. The clinician may then confirm whether the highlighted areas are lesions and provide input to application 81 to mark the confirmed lesions as target locations in the 3D model. The clinician may also select one or more lesions and/or target locations by viewing the image data and/or the 3D model. For example, by using input device 510 and display 506 of computing device 80 (described below with reference to FIG. 5), the clinician may view the image data and/or 3D model and may identify and select one or more lesions and/or target locations. The clinician may also select and/or mark various areas of the image data to identify those areas as areas that may require diagnosis and/or treatment. Thereafter, application 81 may identify and mark one or more locations in the 3D model that correspond to the locations marked by the clinician.

Application 81 may automatically, or with input from the clinician, generate a diagnosis and/or treatment plan, as described further in U.S. Patent Appl. Publ. No. 2016/0038248, noted above. As will be appreciated by those skilled in the art, consistent with the current iLogic™ planning system described in U.S. Patent Appl. Publ. No. 2016/0038248, this treatment plan generation may also occur prior to the generation of the 3D model by simply viewing the image data, without departing from the scope of this disclosure.

After one or more lesions are identified and marked as target locations, the 3D model may be registered with the patient's body, as described above. Thereafter, during the navigation phase, application 81, via EM tracking system 70, tracks the location of EM sensor 94 as a tool, such as LG 92 or tools 62, 64, is navigated about the patient's airways. For example, application 81 receives EM tracking data from EM tracking system 70 regarding the position of EM sensor 94 within the EM field generated by EM field generator 76 and processes the EM tracking data to determine the location of EM sensor 94 within the patient's airways. Those skilled in the art will appreciate that in a percutaneous or laparoscopic embodiment, an EM sensor coupled to tool 230 may similarly be tracked, as described above, without departing from the scope of this disclosure. Application 81 then displays the tracked location of EM sensor 94 on the 3D model, thereby providing an indication of the location of the tool inside the patient's airways. As described above, in some embodiments the navigation phase commences after step S312. Thus, in such embodiments, the tool may already be at the target location or may merely need to be repositioned to the target location. In other embodiments, the navigation phase may first commence after step S322, and thus in such embodiments the above-described steps of the navigation phase may be performed after step S322. In either embodiment, after the tool has been placed at the target location, a lesion at the target location may be injected with a radiopaque element, such as radio-tagged whole blood from the patient, a collagen tracer, a metabolic tracer such as radiolabeled glucose, a radiation tracer or other isotopes such as gallium along with radiolabeled antibodies, and/or radiolabeled gas that may be inhaled by the patient instead of injected.

After the lesion or the lymph node has been injected with the radiopaque element, one or more additional scans of the patient's chest may be performed to acquire second image data of the patient's chest. For example, one or more fluoroscopic and/or ultrasound scans may be performed, but, as mentioned above, those skilled in the art will recognize that other imaging modalities may also be used without departing from the scope of this disclosure. The additional scans may be performed after a period of time has elapsed since the radiopaque element was injected into the lesion to enable the radiopaque element to be spread via the patient's lymphatic system. Application 81 then receives the second image data from the one or more additional scans at step S324.

Thereafter, at step S326, application 81 processes the second image data to identify the radiopaque element injected into the lesion. The identification may be performed using image analysis and processing techniques, similar to those described above. Additionally, application 81 may analyze dynamic regional flow distribution and/or a ventilation/perfusion ratio within the various branches of the vascular and/or lymphatic lumens emanating from the location where the radiopaque element is injected.

Application 81 may then, at step S328, determine whether a drainage/distribution path of the radiopaque element can be detected. For example, application 81 may determine whether the radiopaque element is detectable in a plurality of lymph nodes and/or lymphatic lumens emanating from the lesion where the radiopaque element was injected and/or whether the radiopaque element is detectable in one or more blood vessels draining from the target location. The determination may be based on whether the radiopaque element is detectable in a predetermined number of lymph nodes and/or a predetermined distance from the lesion in lymph ducts and/or blood vessels. The determination may further be based on whether the drainage of the radiopaque element has not spread far enough yet, and/or that the radiopaque element has become too diluted to be detectable. If application 81 determines that a drainage/distribution path of the radiopaque element is not detectable, processing returns to step S326. Application 81 may also cause computing device 80 to display an error message indicating the reason why a drainage/distribution path could not be determined.

Alternatively, if application 81 determines that a drainage/distribution path can be detected, processing proceeds to step S330, where application 81 further processes the second image data to identify a sentinel lymph node in a drainage/distribution path. A sentinel lymph node is a lymph node proximate the lesion from which one or more drainage/distribution paths emanate. After identifying a sentinel lymph node, application 81 may further process the second image data, at step S332, to trace a drainage/distribution path emanating from the sentinel lymph node to identify other lymph nodes in the drainage/distribution path and/or blood vessels draining from an area proximate the sentinel lymph node. The drainage/distribution path may include all lymph nodes along a path in which the radiopaque element can be detected, and all blood vessels draining from areas proximate such lymph nodes. In some embodiments, application 81 may further identify directions of fluid flow in the lymphatic and/or vascular networks both leading to and away from the sentinel lymph node and other lymph nodes identified in the drainage/distribution path and/or the target location. The directions of fluid flow may then be indicated on the lymphatic tree map and/or the vascular tree map. Application 81 may further identify a relationship between the directions of fluid flow in various branches of the lymphatic and/or vascular networks, such as by performing a flow assessment based on weighted averages of the fluid flow and/or flow patterns, etc. At various lymph nodes along the drainage/distribution path, other drainage/distribution paths may branch off from the drainage distribution path being traced. Application 81 may then, at step S334, display the identified lymph nodes in the drainage/distribution path on the lymphatic tree map, and the identified blood vessels draining from such lymph nodes on the vascular tree map.

Thereafter, at step S336, application 81 determines whether all drainage/distribution paths have been traced. For example, application 81 may determine whether additional drainage/distribution paths or branches emanating from the lesion, the sentinel lymph node, or any other lymph node down any of the drainage/distribution paths, have to be analyzed. If additional drainage/distribution paths have to be analyzed, processing returns to step S330. Alternatively, if application 81 determines that all drainage/distribution paths have been analyzed, processing proceeds to step S338.

At step S338, application 81 selects one or more of the lymph nodes identified at steps S330 and/or S332 to be biopsied to determine whether, and how far, disease has spread. For example, application 81 may select the lymph nodes in which the radiopaque element was detected furthest from the lesion. In another example, application 81 may select lymph nodes a predetermined distance from the lesion. For example, application 81 may select lymph nodes which are at least 5 cm from the lesion and/or sentinel lymph node. In another example, application 81 may select lymph nodes which are between 7 cm and 10 cm from the lesion and/or sentinel lymph node. In yet another example, application 81 may select lymph nodes which are at least three lymph nodes removed from the sentinel lymph node down the distribution path, that is, the selected lymph nodes have at least three other lymph nodes in the distribution path between the selected lymph nodes and the sentinel lymph node. Thereafter, at step S340, application 81 displays the lymph nodes to be biopsied on the lymphatic tree map. The lymph nodes to be biopsied may be ranked in an order from most likely to include spread of cancerous cells to least likely. The clinician may then select which lymph nodes to biopsy. Application 81 may further generate and display a navigation plan for navigation a tool to the lymph nodes selected to be biopsied.

Figure 4:
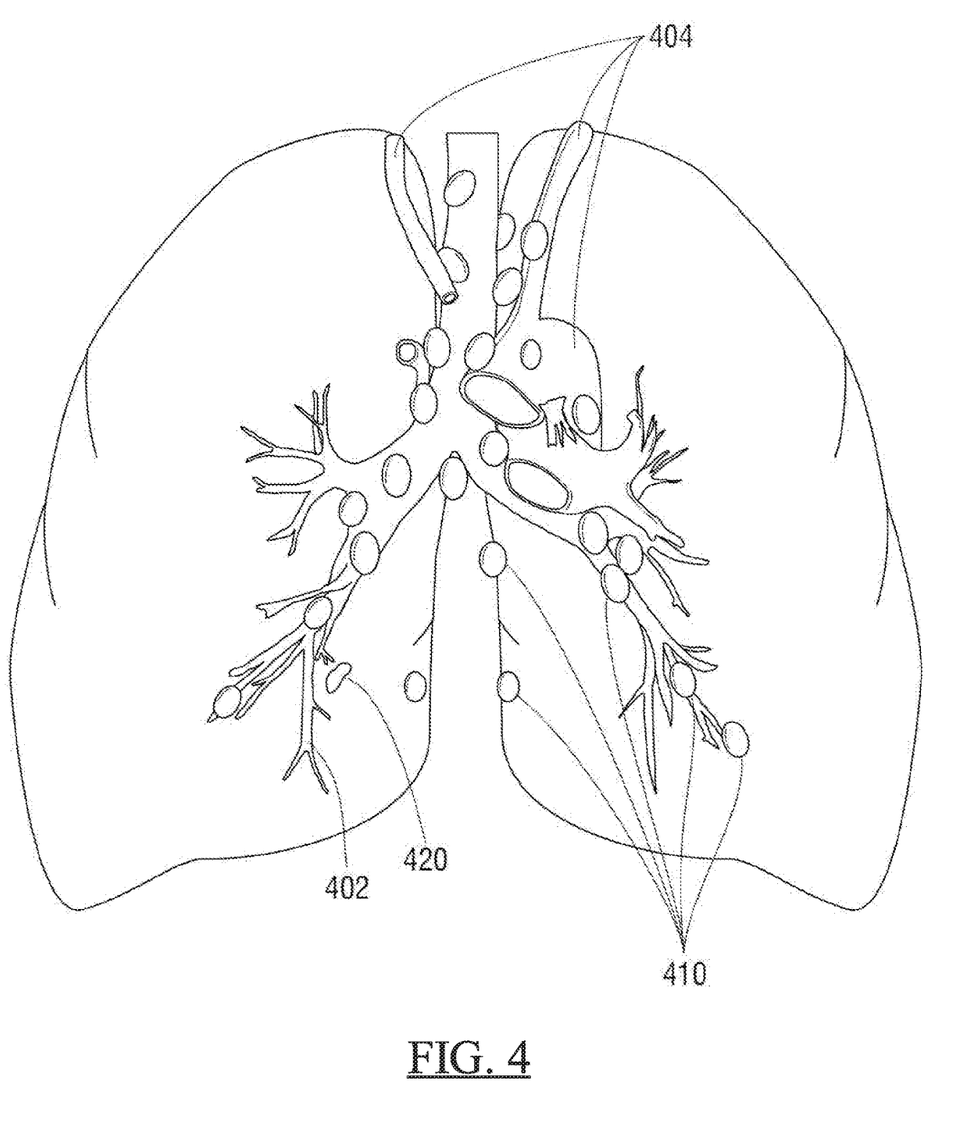
FIG. 4 is an exemplary graphical user interface showing an airway tree and lymphatic tree map, according to an embodiment of the disclosure.

FIG. 4 illustrates an exemplary graphical user interface (GUI) including a 3D model of a patient's chest overlaid with a lymphatic tree map, as described above. The 3D model includes a bronchial tree 402 showing the trachea and the various bifurcations of the airways. The 3D model further includes vascular structures 404, such as major arteries and veins, as well as lymph nodes 410 of the lymphatic tree map, and a selected target location 420. The GUI of FIG. 4 may be displayed by computing device 80 at various stages of the above-described medical procedure, for example, at steps S320, S334, and/or S340.

Figure 5:
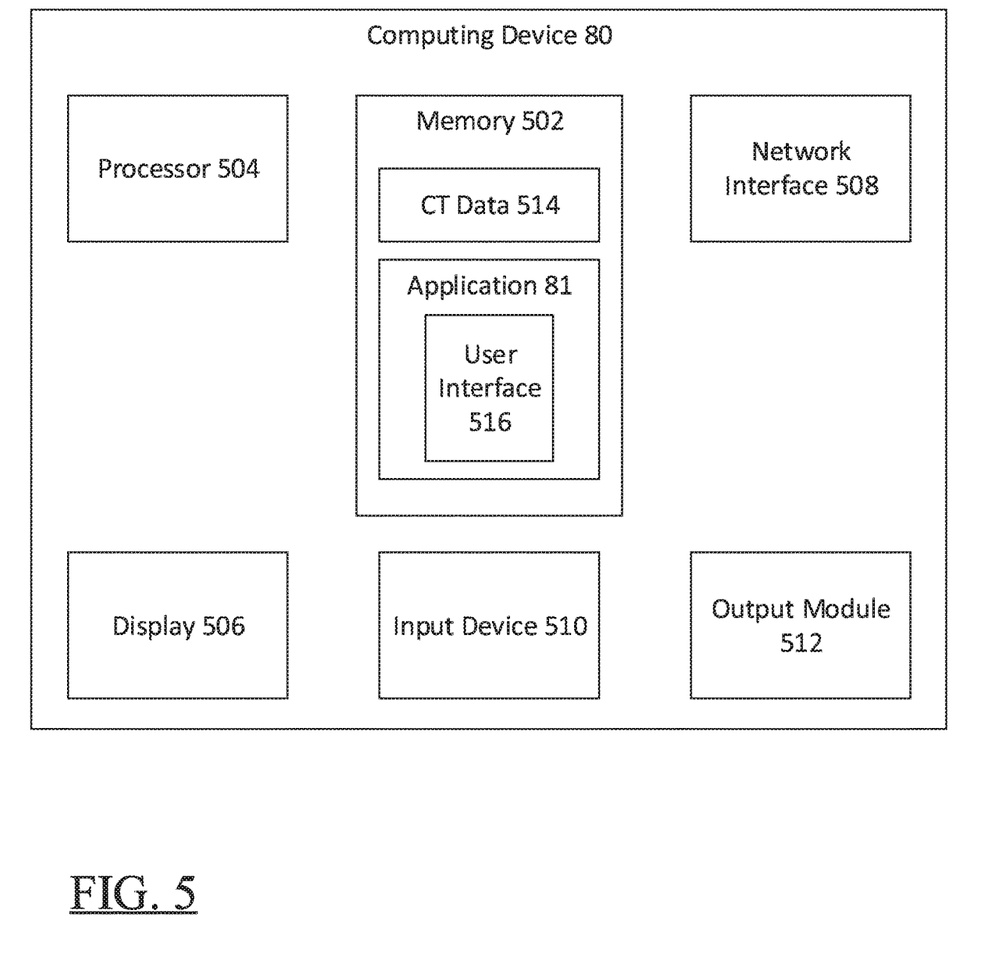
FIG. 5 is a block diagram of an example computing device forming part of the systems of FIG. 1 and/or FIG. 2.

FIG. 5 illustrates a simplified block diagram of computing device 80. Computing device 80 may include a memory 502, a processor 504, a display 506, a network interface 508, an input device 510, and/or an output module 512. Memory 502 may store application 81 and/or image data 514. Application 81 may, when executed by processor 504, cause display 506 to present user interface 516. Application 81 may also provide the interface between the tracked position of EM sensor 94 and the image and planning data developed in the pathway planning phase.

Memory 502 may include any non-transitory computer-readable storage media for storing data and/or software that is executable by processor 504 and which controls the operation of computing device 80. In an embodiment, memory 502 may include one or more solid-state storage devices such as flash memory chips. Alternatively or in addition to the one or more solid-state storage devices, memory 502 may include one or more mass storage devices connected to the processor 504 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 504. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 508 may be configured to connect to a network such as a local area network (LAN) consisting of a wired network and/or a wireless network, a wide area network (WAN), a wireless mobile network, a Bluetooth network, and/or the internet. Input device 510 may be any device by means of which a user may interact with computing device 80, such as, for example, a mouse, keyboard, foot pedal, touch screen, and/or voice interface. Output module 512 may include any connectivity port or bus, such as, for example, parallel ports, serial ports, universal serial busses (USB), or any other similar connectivity port known to those skilled in the art.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ this disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for mapping a patient's lymphatic system, the method comprising:
    generating a three-dimensional (3D) model of a bronchial network in a chest of the patient based on first image data of the chest of the patient;
    generating a lymphatic tree map by fitting a model lymph node map to the 3D model;
    receiving locations of a plurality of identified lymph nodes;
    updating the lymphatic tree map by correlating the locations of the plurality of identified lymph nodes with the lymphatic tree map;
    displaying the updated lymphatic tree map;
    receiving second image data of the chest of the patient;
    identifying a radiopaque element injected into a target in the second image data;
    determining a distribution path from the target based on the radiopaque element identified and the lymphatic tree map as updated;
    identifying a sentinel lymph node based on the distribution path;
    displaying the sentinel lymph node identified on the lymphatic tree map as updated;
    identifying a lymph node in the distribution path a predetermined distance from the sentinel lymph node; and
    displaying the lymph node identified on the lymphatic tree map as updated.

2. The method according to claim 1, wherein the plurality of lymph nodes are identified based on image processing of the first image data.

3. The method according to claim 1, wherein the lymph nodes are identified based on electromagnetic sensor (EM) data received from an EM sensor coupled to a tool being navigated about the chest.

4. The method according to claim 1, wherein the lymph nodes are identified based on return signals received from a linear ultrasound scope.

5. The method according to claim 1, further comprising identifying a lesion in the 3D model.

6. The method according to claim 5, wherein the target is a lymph node proximate the identified lesion.

7. The method according to claim 1, wherein the radiopaque element is one of:
    radio-tagged whole blood from the patient;
    a collagen tracer; and
    a radiation tracer.

8. The method according to claim 1, wherein the predetermined distance is at least about 5 cm.

9. The method according to claim 1, wherein the predetermined distance is between about 7 cm and about 10 cm.

10. The method according to claim 1, wherein the lymph node identified is a lymph node with at least three other lymph nodes between the lymph node identified and the sentinel lymph node.

11. The method according to claim 1, further comprising:
    determining areas to which spread may occur based on the sentinel lymph node identified and the distribution path; and
    displaying the areas to which spread may occur on the lymphatic tree map as updated.

12. The method according to claim 1, wherein the model lymph node map is International Association for the Study of Lung Cancer (IASLC) lymph node map.

* * * * *